United States Patent [19]

McGeeney

[11] 4,337,309
[45] Jun. 29, 1982

[54] METHOD OF DETERINING THE CONCENTRATION OF PANCREATIC AND SALIVARY α-AMYLASE IN BODY FLUIDS

[75] Inventor: Kevin F. McGeeney, Dublin, Ireland

[73] Assignee: Pharmacia Diagnostics AB, Sweden

[21] Appl. No.: 154,041

[22] Filed: May 28, 1980

Related U.S. Application Data

[63] Continuation of Ser. No. 882,228, Feb. 28, 1978, abandoned.

[51] Int. Cl.³ .......................... C12Q 1/40; C12N 9/99
[52] U.S. Cl. ........................................ 435/22; 435/184
[58] Field of Search .......................... 435/22, 184, 810; 424/2

[56] References Cited

U.S. PATENT DOCUMENTS 4,000,042 12/1976 Adams ................................ 435/22

OTHER PUBLICATIONS

O'Donnell, et al., "Differential Serum Amylase Determination by Use of an Inhibitor, and Design of a Routine Procedure", *Clin Chem.*, vol. 23, No. 3, (1977), pp. 560-566.
O'Donnell, et al., "Purification and Properties of an α-Amylase Inhibitor from Wheat", *Biochem Biophys*, Acta., vol. 422 (1976), pp. 159-169.

Bergmeyer, *Methods of Enzymatic Analysis*, vol. 2, Academic Press, Inc., New York, (1974), pp. 885-915.
Wilkinson, *The Principles and Practices of Diagnostic Enzymology*, Yearbook Medical Publishers, Inc., Chicago (1976), pp. 149-154.

*Primary Examiner*—Thomas G. Wiseman
*Attorney, Agent, or Firm*—Bacon & Thomas

[57] ABSTRACT

A method of determining the concentration of pancreatic α-amylase and salivary α-amylase in a body fluid containing a mixture of said α-amylases. First and second samples of said body fluid are prepared, and the second samples are treated with an effective amount of an inhibitor capable of selectively inhibiting the activity of said α-amylases. The amount of total α-amylase, i.e. the sum of salivary α-amylase and pancreatic α-amylase, is then measured for said first and second samples, and the concentration of salivary and pancreatic α-amylase present in said first and second samples is determined by comparing the measured total α-amylase values with a standard. The inhibitor used has a discrimination factor—expressed as the ratio between the quantity of inhibitor necessary for reducing the activity of one of said two α-amylases by 50% and the quantity of inhibitor necessary for reducing the same activity of the other of said α-amylases by 50%—of at least 20:1, preferably at least 50:1, and especially at least 80:1.

6 Claims, 2 Drawing Figures

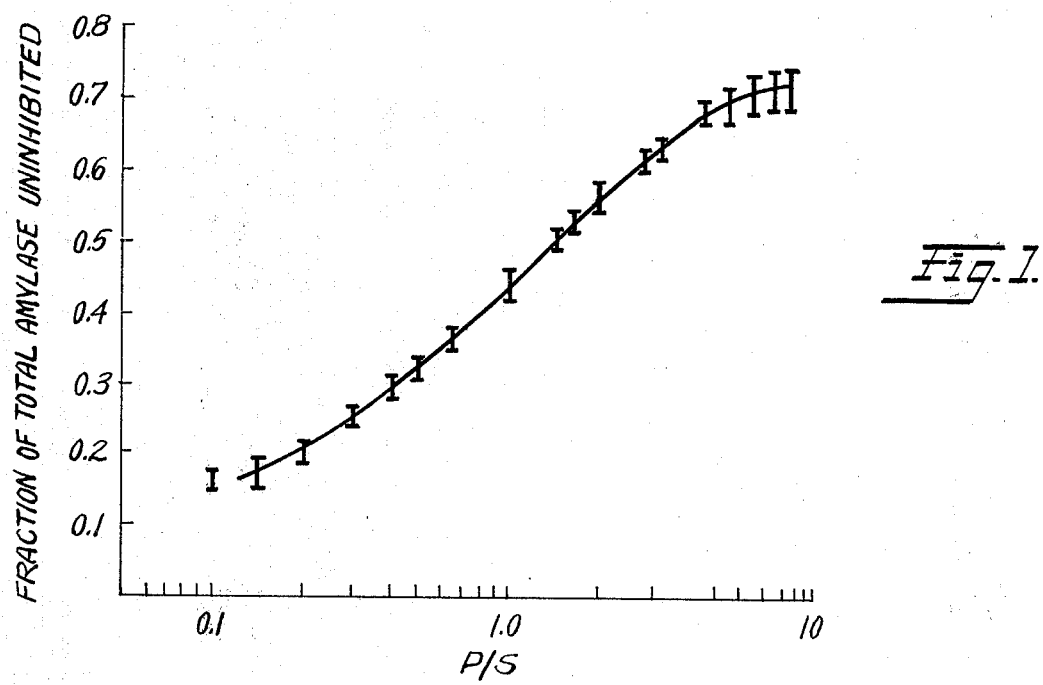

STANDARD CURVE OBTAINED BY MIXING PURIFIED PANCREATIC AND SALIVARY AMYLASE IN P/S RATIOS IN THE RANGE 0.1-8 AND ANALYZING THE MIXTURES FOR AMYLASE ACTIVITY IN THE PRESENCE AND ABSENCE OF INHIBITOR (0.5 µg PER TUBE)
EACH POINT IS THE MEAN OF AT LEAST 5 ANALYSES.
THE BARS INDICATE ± 2SD

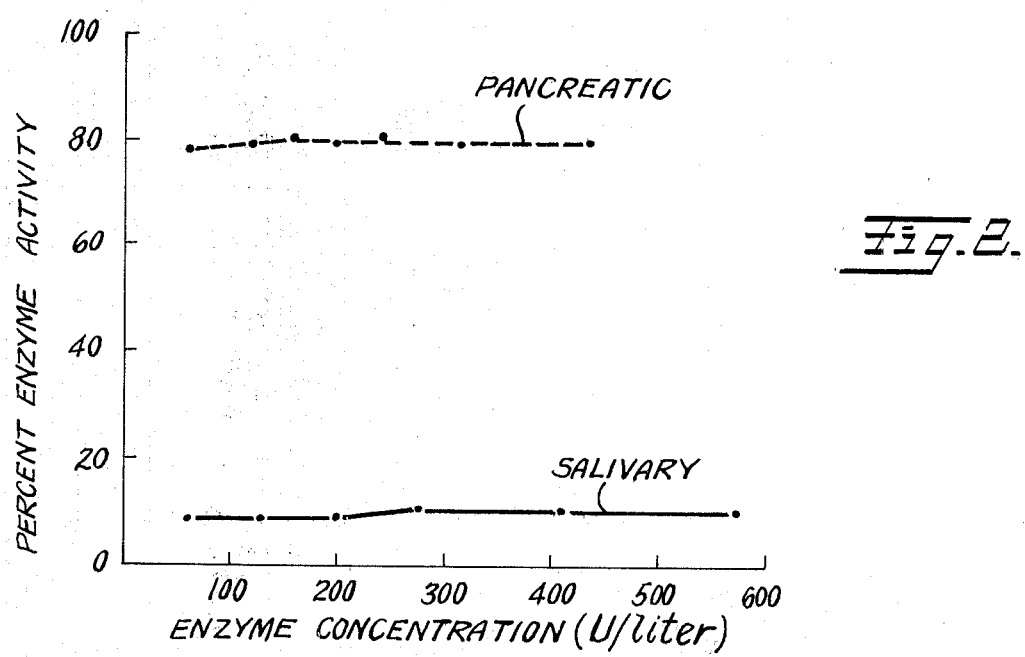

EFFECT OF A CONSTANT AMOUNT OF INHIBITOR (0.5 µg) ON VARIOUS PANCREATIC AND SALIVARY AMYLASE ACTIVITIES

METHOD OF DETERINING THE CONCENTRATION OF PANCREATIC AND SALIVARY α-AMYLASE IN BODY FLUIDS

This is a continuation of application Ser. No. 882,228, filed Feb. 28, 1978, abandon.

BACKGROUND OF THE INVENTION

It is known that many pathologic conditions cause changes in the α-amylase levels in body fluids such as serum, urine, etc., and diagnostic methods for measuring the α-amylase concentration in body fluids have been developed. These methods are usually based on the degrading effect of α-amylase on starch products, the enzyme activity being determined by measuring—directly or indirectly—the degree of degradation of a starch-like substrate. Examples of such known methods are the so-called "blue starch method" and the so-called "saccharogenic method". In the first mentioned method the substrate is insoluble, cross-linked starch, whereas soluable (Zulkowsky) starch is used in the saccharogenic method. These and other methods for measuring the α-amylase concentration in body fluids are well known in the art. See e.g. O'Donnell and Mc. Geeney, Comparison of Saccharogenic and Phadebas ® methods for amylase assay in biological fluids, Enzyme 18, 348 (1974), and Robyt and Whelan in Starch and its derivatives, 4th Ed. J. A. Radley, Ed. Chapman and Hall, London 1968 pp. 431–433.

Although these methods for determining α-amylase activity have proved to be valuable aids in discovering α-amylase levels in body fluids, they have certain limitations. In particular, these methods do not discriminate between the pancreatic and salivary types of α-amylase. Thus, only the total α-amylase activity, i.e. the sum of the salivary α-amylase activity and the pancreatic α-amylase activity, can be determined by these methods.

It would in many diagnostic situations be highly desirable not only to determine the total α-amylase concentration in body fluids, but also to separate between the two components thereof, i.e. salivary α-amylase and pancreatic α-amylase. In this manner it would be possible to discover hyper- or hypofunctioning states of pancreas or salivery glands, reflecting pathologic conditions such as pancreatitis (increased pancreatic α-amylase activity), ruptured ectopic pregnancy (increased salivary α-amylase activity), and others. It may also be mentioned, that a seemingly "normal" total α-amylase content of a body fluid may be composed of an abnormally high amount of one of the two enzymes and an abnormally low amount of the other.

Thus, there is a great need for rapid and reliable diagnostic methods, making it possible to determine the pancratic as well as the salivary α-amylase activity in body fluids. However, the gross similarity between these two enzymes has caused difficulties in measuring either of them in the presence of the other, and immunological methods of distinguishing between them have been unsuccessful. Pancreatic and salivary α-amylase can be separated by electrophoretic, electrofocusing or chromatographic methods [see E. G. S. Norby, Electrophoretic non-identity of human salivary and pancreatic amylases, Exp. Cell Res. 36; 663 (1964); Takeuchi, Matsushima and Sugimura, Separation of human α-amylase isoenzymes by electrofocusing and their immunologic properties, Clin. Chim. Acta 60, 207 (1975); Beck and Fridhandler, Clinical application of amylase isoenzyme analysis, Am. J. Gastroenterol 63, 457 (1975)]. However, these methods have the disadvantage of being tedious and time consuming.

BRIEF SUMMARY OF THE INVENTION

It is an object of the present invention to eliminate or reduce the disadvantages of the prior art methods and to provide a rapid, simple and reliable method of determining the pancreatic α-amylase and salivary α-amylase levels in body fluids containing a mixture of said α-amylases.

According to the invention first and second samples of a body fluid to be analyzed are prepared and the total α-amylase activities thereof are determined by means of any suitable method of determining total α-amylase activity, such as the above mentioned blue starch method or saccharogenic method. Before measuring the total α-amylase activity of said second samples, an effective amount of an inhibitor capable of selectively inhibiting the activity of said α-amylases is added to said samples. Said inhibitor should have a discrimination factor of at least 20:1, preferably at least 50:1, and especially at least 80:1, expressed as the ratio between the quantity of inhibitor necessary for reducing the activity of one of said two α-amylases by 50% and the quantity of inhibitor necessary for reducing the same activity of the other of said α-amylases by 50%. The salivary and pancreatic α-amylase levels of said samples are then determined by comparing the measured values for total α-amylase of said first and second samples with a standard.

According to a first embodiment of the invention said standard is a standard curve, prepared by adding said effective amount of inhibitor to a number of samples containing known proportions (P/S) of pancreatic (P) and salivary (S) α-amylase, measuring the fraction of total α-amylase uninhibited for each of said samples, and plotting said measured values versus the known P/S ratios. It has unexpectedly been discovered that the fraction of α-amylase uninhibited is proportional to the P/S ratio within a broad range of P/S ratios, and as the total amount of α-amylase of the tested samples is made up of salivary plus pancreatic α-amylase levels, the latter can easily be determined; see Example 2(c) below.

According to an alternative embodiment of the invention the degree of inhibition caused by the effective amount of inhibitor used is determined for standards containing only pancreatic α-amylase and salivary α-amylase respectively, the activities of the standards being chosen to be as near as possible to the activities of the unknown samples, i.e. of the same order of magnitude. It has unexpectedly been found that the degree of inhibition caused by a constant amount of inhibitor is constant over a broad range of pancreatic as well as salivary α-amylase activities. As a result, the pancreatic and salivary α-amylase levels of unknown body fluid samples can easily be calculated from the measured total α-amylase levels, with and without addition of inhibitor, once the degree of inhibition of the pancreatic and salivary α-amylases standards have been determined; see Example 3 below.

It should in this connection be mentioned that the α-amylase activity of the sample to be tested should be adjusted so as to fall within the range where the degree of inhibition is constant for both pancreatic and salivary α-amylase. This adjustment can be made by simple dilution of the tested samples, where necessary (e.g. when the undiluted sample points to too high α-amylase levels when tested). In practice this is only a minor problem, as the range of permitted α-amylase levels is comparatively broad and covers most expected variations of the α-amylase levels, provided that a suitable inhibitor and a suitable effective amount thereof have been chosen.

In the method according to the invention any type of inhibitor can be used, provided that it is capable of discriminating between pancreatic and salivary α-amylase (and vice versa) to the degree defined above. The preferred inhibitors are obtained by extraction of cereal grains, especially wheat seeds, and the especially preferred inhibitor has a discrimination factor of about 100:1.

The effective amount of inhibitor used varies depending on such factors as the specific inhibitor used and the discrimination factor thereof, and this amount is chosen so as to cause greatest possible inhibition of one of the α-amylases and smallest possible inhibition of the other α-amylase. The effective amount of inhibitor is preferably chosen such that it causes a constant degree of inhibition for both pancreatic and salivary α-amylase at enzyme concentrations ranging from about 50 to about 600 U/liter, corresponding to the preferred range of enzyme activity of the samples to be tested.

The method according to the invention is not restricted to quantitative analysis, but it also includes semi-quantitative determination of the pancreatic and salivary α-amylase levels, i.e. determination of whether or not a body fluid sample has a normal pancreatic to salivary α-amylase ratio.

DESCRIPTION OF PREFERRED EMBODIMENTS OF THE INVENTION

The method according to the invention is further illustrated in the following non-limiting examples.

EXAMPLE 1

An inhibitor with much greater specificity for human salivary α-amylase than for human pancreatic α-amylase was isolated from wheat seeds, purified and analyzed as follows (see also O'Donnell and Mc. Geeney, Purification and properties of an α-amylase inhibitor from wheat, Biochimica et Biophysica Acta 422 (1976), 159–169).

Extraction and separation of α-amylase inhibitors

Aqueous extract

Wheat seeds (400 g) of Triticum aestivum species were finely ground and suspended in $H_2O$ (1:3, w/v), stirred (1 h) and filtered. The residue was washed again with 1 vol. $H_2O$, stirred (30 min.) and filtered. The clear supernatants were pooled and freeze-dried. The resulting powder (28 g) was stored at room temperature and used as starting material in the purification procedure. An aliquot of this product was dissolved in $H_2O$ (1:10, w/v), heated at 70° C. (30 min.) to inactivate α- and β-amylases, cooled and centrifuged (8000×g, 10 min). The precipitate was discarded.

Alcohol fractionation

The aqueous extract was treated with absolute alcohol to 60% saturation (20° C.). The inactive precipitate was separated by centrifugation (8000×g, 30 min) and discarded. The alcohol concentration was raised to 90% saturation and the resulting precipitate, which contained the α-amylase inhibitory activity, was separated by centrifugation as above. This precipitate (referred to hereafter as the alcohol fraction) was washed three times with absolute alcohol and allowed to dry overnight at 30° C.

Ion-exchange chromatography

The alcohol fraction was dissolved in Tris.HCl buffer (I=0.02, pH 9.2 containing 2 mM NaCl) and dialysed overnight against same buffer. Any cloudiness that developed was removed by centrifugation (3000×g, 10 min). The supernatant was applied to a QAE-Sephadex ® A-50 column (50 cm×1.5 cm; a diethyl-(2-hydroxypropyl)aminoethyl-substituted cross-linked dextran gel, available from Pharmacia Fine Chemicals AB, Uppsala, Sweden) previously equilibrated with above buffer. 3 column volumes of buffer (pH 9.2) were eluted prior to any change in buffer pH. The pH was reduced stepwise keeping the ionicity constant. 6-ml fractions were collected at a flow rate of 20–24 ml.h$^{-1}$ and analysed for inhibition of both salivary and pancreatic amylases as described below. The fractions containing the first inhibitor peak which emerged from the column at pH 8.9 were pooled, concentrated to 5 ml by ultrafiltration (Amicon UM 2 membrane), adjusted to pH 9.2, diluted with an equal volume of $H_2O$ and applied to a DE52-cellulose column (13 cm×1 cm) previously equilibrated with Tris-HCl buffer (I=0.01, pH 9.2 containing 1 mM NaCl). Following application of the inhibitor solution, 5 column volumes of buffer were eluted before starting the NaCl (0–0.1 M) gradient. 2.5-ml fractions were collected. The fractions containing the inhibitor were pooled on analysis and concentrated (Amicon UM 2 membrane) prior to gel filtration. Protein was monitored in all chromatographic fractions by measurement of absorbance at 280 nm on an LKB Uvicord II.

Gel filtration 2 ml of inhibitor solution from DE52-cellulose peak were loaded on a Sephadex ® G-50 column (62 cm×2 cm; a cross-linked dextran gel, available from Pharmacia Fine Chemicals AB, Uppsala, Sweden) and eluted with a 1 mM phosphate buffer (pH 6.9) containing 0.1 M NaCl and 0.5 mM $CaCl_2$ at a flow rate of 12 ml.h$^{-1}$.1.9-ml fractions were collected and tested for inhibitor activity.

Analytical determinations

Enzyme assay

The source of salivary α-amylase was saliva collected from laboratory personnel, and the source of pancreatic α-amylase was post mortem pancreatic tissue from patients who had not suffered pancreatic damage or functional disturbance. α-Amylase activity was measured by the Phadebas ® blue starch method and incorporating albumin (7.4 μM) in the reaction mixture for optimal amylase activity. Since salivary and pancreatic amylases hydrolyse insoluble starches at different rates calibration curves for both enzymes were prepared. The amylase unit (I.U) is defined as that activity which liberates reducing groups corresponding to 1 μmol of maltose/min at 37° C.

Inhibition of α-amylase

The inhibitor solution (10–50 μl) containing 0.1–10 μg protein was added to 0.4 ml of buffer (50 mM phosphate, 50 mM NaCl, 0.5 mM $CaCl_2$, pH 6.9) containing 2 mg albumin, followed by 0.1 ml of amylase solution (42–52 munits) in above buffer. This mixture was incubated at room temperature for 30 minutes. Enzyme and inhibitor were pre-incubated (30 min) in all assays unless stated otherwise. The volume was made up to 4.1 ml with water, for analysis of remaining amylase activity in a 15 min. incubation (37° C.) period. A control tube was set up without the addition of inhibitor. The quantity of inhibitor used was that which reduced the amylase activity by 50%. This is because the plot of salivary amylase activity vs. inhibitor concentration is linear in the region of 50% reduction of enzyme activity. The inhibitor unit is defined as the quantity of inhibitor required to reduce the activity of 2 I.U. of amylase by 50% i.e. 1 unit of inhibitor inhibits 1.0 I.U. of enzyme under these conditions. The ratio of inhibitor activity towards human salivary amylase relative to human pancreatic amylase is referred to as the salivary/pancreatic ratio.

Results for serum in the blank tube. Absorbances at 620 nm were measured with a Cecil CE 272 spectrophotometer (Cecil Instruments Ltd., Cambridge, U.K.). Total amylase values for both tubes were read off a standard curve, prepared by determining absorbances at 620 nm for samples with known concentrations of human pancreatic and salivary α-amylase (determined by the saccharogenic method) and plotting these absorbance values versus the known α-amylase concentrations. In the case of too high amylase values the serum was diluted with albumin (100 g/liter) before analysis, and the appropriate dilution factor applied. The value for total serum amylase ($A_{tot}$) was obtained from the tube without inhibitor added. Amylase remaining in the presence of the inhibitor ($A_{res}$) was obtained from the absorbance values given by the tube containing the inhibitor and calculated from the standard curve. The fraction of amylase uninhibited, $A_{res}/A_{tot}$, is proportional to the P/S ratio of the sample, as illustrated by the P/S standard curve.

TABLE I

| Purification step | Vol. (ml) | Total salivary amylase inhibitory units | Total protein (mg) | Specific activity (units/mg protein) | HS/HP inhibitor activity ratio** | Recovery from previous step (%) |
|---|---|---|---|---|---|---|
| Aq. extract of wheat seed, freeze-dried 1.9 g | 19 | 17 800 | 445 | 40 | 4.0 | — |
| Aq. extract post heating (70° C., 30 min) | 19 | 17 000 | 320 | 55.5 | 4.0 | 96 |
| Alcohol fraction (60–90%) 0.5 g | 10 | 8 800 | 156 | 60 | 3.7 | 49.5 |
| Peak 1 Inhibitor from QAE-Sephadex ® A-50 | | 1 375 | | | | 15.6 |
| Conc. peak fractions | 10 | 800 | 14.4 | 55.5 | 91 | 9.1 |
| Inhibitor fractions from DE52-Cellulose column | | 586 | | | | 42.6* |
| peak fractions | 7.5 | 407 | 5.75 | 71 | 100 | |
| Sephadex ® G-50 | 24 | 272 | | | | 19.8* |
| G-50 peak fractions post Amicon (UM 2) ultra-filtration | 4.8 | 135 | 0.55 | 245 | 100 | 9.8* |

*Calculated on figure of 1375 obtained from QAE-Sephadex peak.
**The inhibition activity of the various fractions against human pancreatic amylase was measured after each step. The human salivary amylase inhibitory units divided by the human pancreatic amylase inhibitory units = HS/HP inhibitor activity ratio.

The yield and potency of various of the fractions obtained are summarized in Table I below.

EXAMPLE 2

Determination of salivary (S) and pancreatic (P) α-amylase levels in serum samples (a) Procedure Into each of two 10-ml glass centrifuge tubes were added, in the order given, 0.3 ml of phosphate buffer (pH 6.9, 50 mmol/liter) containing 50 mmol/liter NaCl and 0.5 mmol/liter $CaCl_2$, followed by 0.2 ml of human serum to be analyzed. The mixture was shaken gently by hand and then 10 μl of inhibitor solution, prepared according to Example 1, was added to one tube and the contents mixed again. All tubes were pre-incubated at 20° C. (room temperature) for 25 minutes. This allows for maximum inhibition of salivary amylase in the tube containing the inhibitor. The reaction mixtures were then diluted to 4.1 ml with distilled water and both tubes were analyzed for total α-amylase activity by the Phadebas ® blue starch method in a 15 minutes (37° C.) incubation procedure. Albumin (10 mg) was substituted (b) Construction of P/S standard curve Purified human salivary and pancreatic amylase were mixed in phosphate buffer (as above) to give P/S ratios in the range 0.1–8.0. Enzyme activities ranged from 50 to 200 U/liter (pancreatic) and 20 to 400 U/liter (salivary). These mixtures were made up immediately before use. They were analyzed for α-amylase in the presence and in the absence of inhibitor as follows. To duplicate 10-ml glass centrifuge tubes the following additions were made, with gentle shaking by hand between each addition: 0.2 ml of phosphate buffer (composition as above), 0.1 ml of amylase free serum, and 0.2 ml of amylase mixture (P+S). Inhibitor solution (10 μl) was added to the tube for pancreatic amylase assay. The tube without added inhibitor is used to find the total amylase value. α-Amylase-free serum (0.1 ml) was included in the reagent blank. The 25-min. pre-incubation, 15-min. incubation, and absorbance readings were all done as above. α-Amylase activities were calculated for the solution in the presence and absence of inhibitor. The fraction of amylase uninhibited ($A_{res}/A_{tot}$) was calculated for each tube. This value was plotted against the known P/S ratio, as in FIG. 1 below. As can be seen from this Figure the $A_{res.}/A_{tot.}$ ratio is proportional to the P/S ratio.

(c) Calculation of serum pancreatic (P) amylase

Total serum α-amylase, $A_{tot.}$, is made up of salivary plus pancreatic, i.e.

$$A_{tot.} = P + S \quad (1)$$

The ratio P/S is known from FIG. 1.

$$\text{Let } P/S = R \quad (2)$$

substituting P/R for S in equation 1 we get $$A_{tot.} = P + P/R \quad (3)$$

$$= P(1 + 1/R)$$

$$\therefore P = \frac{A_{tot.}}{1 + 1/R}$$

Since $P/S = R$, $$P = \frac{A_{tot.} \times P/S}{1 + P/S} \quad (4)$$

Salivary α-amylase activity is then found by substituting the value obtained for P in equation 1, i.e.

$$S = A_{tot.} - P$$

(In equations (1)–(4) S may be substituted for P, and vice versa)

EXAMPLE 3

The procedure of Example 2(a) was repeated, but instead of constructing a P/S standard curve according to Example 2(b), human pancreatic α-amylase and human salivary α-amylase standards were included in each batch of analysis for determining the fraction of salivary α-amylase and pancreatic α-amylase resp., uninhibited by the specific amount of inhibitor added. The activities of the standards were selected to be of the same order of magnitude as the activities of the serum samples to be tested (as in Example 2a the serum samples were diluted if the α-amylase values thereof were found to be too high). The α-amylase remaining in the presence of the inhibitor ($A_{res.}$) is made up of the fraction of salivary α-amylase uninhibited ($a_s$) plus the fraction of pancreatic α-amylase uninhibited ($a_p$), i.e.

$$A_{res.} = a_s \cdot S + a_p \cdot P \quad (5)$$

Since $A_{tot.} = S + P$, then $$A_{res.} = a_s(A_{tot.} - P) + a_p \cdot P \rightarrow \quad (6)$$

$$\rightarrow P = \frac{A_{tot.} \cdot a_s - A_{res.}}{a_s - a_p} \quad (7)$$

Since $A_{tot.}$ and $A_{res.}$ have been found by analysis and $a_s$ and $a_p$ are constants determined by the standards, the pancreatic component of the serum samples can be calculated by equation (7).

EXAMPLE 4

In order to demonstrate that the degree of inhibition is constant over a broad range of expected pancreatic and salivary α-amylase concentrations at fixed concentration of inhibitor, samples containing known concentrations of human salivary and pancreatic α-amylase respectively were treated with a constant amount (0.5 μg) of the inhibitor prepared according to Example 1. The degree of inhibition was for each sample determined by means of the blue starch method, expressed as percent enzyme activity, and plotted versus the respective enzyme concentration. As can be seen from FIG. 2 below, the degree of inhibition is constant both for salivary α-amylase (90% inhibition; $a_s = 0.1$) and pancreatic α-amylase (20% inhibition; $a_p = 0.8$) over the range of enzyme concentrations tested.

EXAMPLE 5

The precision of the analyses of pancreatic and salivary type α-amylases by means of the method according to the invention was determined by within-day and day-to-day replicate determinations of three serum samples of different enzyme levels. The "normal" sample was pooled normal serum. The "high S" sample was pooled normal serum with added salivary α-amylase, and the "high P+S" sample was pooled normal serum with added pancreatic and salivary α-amylase. The precision data, which are reported in Table 2 below, attest to the reproducibility of the method.

EXAMPLE 6

Sera from patients suffering from pancreatic insufficiency (including six patients with confirmed cystic fibrosis and five adults with a history of pancreatic exocrine insufficiency) were analyzed for total α-amylase, pancreatic α-amylase, and salivary α-amylase by means of the method according to the invention. Unknown samples of high α-amylase activity were prediluted so that the final extinction value at 620 nm (blue starch method) did not exceed 0.4. Serum samples were stored at −20° C. before analysis. In all cases the total serum α-amylase was within normal limits, i.e. within 2 SD's of the controls. When the values were compared with those of the control group via the Student's t-test the difference obtained was not statistically significant (0.05 < P < 0.1). The mean (U/liter) of serum pancreatic α-amylase levels, 25.9±16.1 (SD), was significantly lower than the figure of 82.4±29.9 for the 72 male controls (P < 0.0005). In addition, the mean for salivary α-amylase activity in pancreatic insufficiency patients was significantly higher than for the controls-80±35.4 (SD) as compared with 49.6±30.4 (P < 0.0025). The test results are reported in Table 3 below.

TABLE 2

Precision of Pancreatic- and Salivary-Type Amylase Assay of Three Pooled Sera

| | | U/liter | | |
|---|---|---|---|---|
| | n | Mean | SD | CV % |
| Day-to-day precision | | | | |
| P-type amylase | | | | |
| Normal amylase | 18 | 84.7 | 3.53 | 4.16 |
| High S serum | 19 | 82.2 | 4.06 | 4.94 |
| High P + S serum | 17 | 312.4 | 17.43 | 5.58 |
| S-type amylase | | | | |
| Normal serum | 18 | 43.0 | 4.17 | 9.7 |
| High S serum | 19 | 204.9 | 7.8 | 3.8 |
| High P + S serum | 17 | 277.2 | 16.6 | 6.0 |
| Within-day precision | | | | |

TABLE 2-continued

Precision of Pancreatic- and Salivary-Type Amylase Assay of Three Pooled Sera

|  | | U/liter | | |
| --- | --- | --- | --- | --- |
|  | n | Mean | SD | CV % |
| P-type amylase | | | | |
| Normal serum | 15 | 86.3 | 3.43 | 3.98 |
| High S serum | 14 | 80.4 | 3.41 | 4.24 |
| High P + S serum | 17 | 304.5 | 10.74 | 3.53 |
| S-type amylase | | | | |
| Normal serum | 15 | 41.5 | 3.25 | 7.82 |
| High S serum | 14 | 208.7 | 10.34 | 4.95 |
| High P + S serum | 17 | 252.4 | 15.7 | 6.22 |

Purified S amylase was added to an aliquot of pooled normal serum to give the high S sample. Purified P and S amylases were added to pooled normal serum to give the high P + S sample. Each pool was held at −20° C. in aliquots before analysis.

TABLE 3

Differential Serum Amylase Activities in Patients with Pancreatic Insufficiency, as Compared with Values for Men Controls.

|  | No. analyses | Mean ± SD(U/liter) | | |
| --- | --- | --- | --- | --- |
|  |  | Total amylase | Pancreatic | Salivary |
| Controls | 72 | 131.9 ± 49.8 | 82.4 ± 29.9 | 49.6 ± 30.4 |
| Pancreatic insufficiency | 11 | 105.7 ± 41.7 | 25.9 ± 16.1 | 80.0 ± 35.4 |
| Significance[a] |  | 0.05 < P < 0.1 | P < 0.0005 | P < 0.0025 |

[a] t-test

What I claim is:

1. A method of determining the levels of pancreatic α-amylase and salivary α-amylase in a body fluid containing a mixture of said α-amylases, comprising the following steps:
   (a) determining the total α-amylase level ($A_{tot.}$) of a first sample of said body fluid by measuring the total α-amylase activity thereof;
   (b) adding to a second sample of said body fluid an inhibitor capable of selectively inhibiting the activity of said α-amylases which inhibitor is obtained by the extraction of cereal grains, in an amount which is effective in inhibiting the activity of a fraction of said α-amylases, said effective amount of said inhibitor being chosen such that it causes a constant degree of inhibition for both pancreatic and salivary α-amylase at total enzyme concentrations ranging from about 50 to about 600 μ/liter; said inhibitor having a discrimination factor, expressed as the ratio between the quantity of inhibitor necessary for reducing the activity of one of said two α-amylases by 50% and the quantity of inhibitor necessary for reducing the same activity of the other of said α-amylases by 50%, of at least 20:1,
   (c) determining the level of total α-amylase uninhibited ($A_{res.}$) in said second sample by measuring the total α-amylase activity thereof, the total enzyme concentration of said first and said second body fluid samples being adjusted, where necessary so as to be within the range from about 50 to about 600 μ/liter;
   (d) establishing the fraction of total α-amylase uninhibited ($A_{res.}/A_{tot.}$), said fraction being proportional to the ratio (P/S) of the pancreatic α-amylase level (P) to the salivary α-amylase level (S) over a broad range of expected P/S ratios; and
   (e) determining the pancreatic α-amylase level (P) and the salivary α-amylase level (S) by comparing said fraction ($A_{res.}/A_{tot.}$) with a standard obtained by performing steps (a), (b), (c), and (d) using a plurality of standard samples each having a different known P/S ratio.

2. A method according to claim 1, wherein the standard used in step (e) is a standard curve obtained by plotting said fraction values versus the corresponding known P/S ratios.

3. A method according to claim 1, further comprising the step of diluting said first and second body fluid samples for adjusting the total α-amylase concentration thereof to fall within the desired range of measurement.

4. A method according to claim 1, wherein the total α-amylase activity is measured by the blue starch method.

5. A method of determining the levels of pancreatic α-amylase and salivary α-amylase in a body fluid containing a mixture of said α-amylases, comprising the following steps:
   (a) determining the total α-amylase level ($A_{tot.}$) of a first sample of said body fluid by measuring the total α-amylase activity thereof;
   (b) adding to a second sample of said body fluid an inhibitor capable of selectively inhibiting the activity of said α-amylases which is obtained by extraction of cereal grains in an amount which is effective in inhibiting the activity of a fraction of said α-amylases, said effective amount of said inhibitor being chosen such that it causes a constant degree of inhibition for both pancreatic and salivary α-amylase at total enzyme concentrations ranging from about 50 to about 600 μ/liter; said inhibitor having a discrimination factor, expressed as the ratio between the quantity of inhibitor necessary for reducing the activity of one of said two α-amylases by 50% and the quantity of inhibitor necessary for reducing the same activity of the other of said α-amylases by 50%, of at least 20:1
   (c) determining the level of total α-amylase uninhibited ($A_{res.}$) in said second sample by measuring the total α-amylase activity thereof, the total enzyme concentration of said first and said second body fluid samples being adjusted, where necessary so as to be within the range from about 50 to about 600 μ/liter;
   (d) subjecting standard samples containing pancreatic α-amylase but not salivary α-amylase and standard samples containing salivary α-amylase but not pancreatic α-amylase respectively to steps (a), (b), and (c) for determining the uninhibited fraction of the respective α-amylases when treated with said effective amount of inhibitor, said standards having α-amylase activities of the same order of magnitude as the activities of the test samples, said uninhibited fractions of the respective α-amylases being constant over a broad range of both pancreatic α-amylase and salivary α-amylase activities, thereby making it possible to calculate the unknown pancreatic and salivary α-amylase levels by the following equations:

$$X = \frac{A_{tot.} \cdot a_y - A_{res.}}{a_y - a_x} \quad \text{(I)}$$

$$A_{tot.} = X + Y \quad \text{(II)}$$

wherein $A_{tot.}$ and $A_{res.}$ are as defined above, X and Y are the unknown levels of the respective α-amylases, and $a_x$ and $a_y$ are the uninhibited fractions of the respective α-amylase as determined by means of said standard samples.

6. A method according to claim 5, further comprising the step of diluting said first and second body fluid samples for adjusting the total α-amylase concentration thereof to fall within the desired range of measurement.

* * * * *